United States Patent [19]

Flamand

[11] 4,033,172

[45] July 5, 1977

[54] APPARATUS FOR TESTING HOLLOW BODIES

[75] Inventor: Guy Flamand, Champforgeuil, France

[73] Assignee: Carnaud Total Interplastic, Chalon-sur-Saone, France

[22] Filed: Dec. 24, 1975

[21] Appl. No.: 644,034

[30] Foreign Application Priority Data

Dec. 30, 1974 France .............. 74.43298

[52] U.S. Cl. ........................... 73/37; 73/45
[51] Int. Cl.² ........................... G01M 3/02
[58] Field of Search ............. 73/37, 45, 45.1, 45.2, 73/45.3, 49.2, 49.3

[56] References Cited

UNITED STATES PATENTS

| | | | |
|---|---|---|---|
| 2,352,091 | 6/1944 | Fedorchak et al. | 73/45.3 |
| 3,010,310 | 11/1961 | Rowe | 73/45 |
| 3,595,065 | 7/1971 | Scribner | 73/37 |

FOREIGN PATENTS OR APPLICATIONS

| | | | |
|---|---|---|---|
| 695,547 | 9/1930 | France | 73/37 |
| 2,033,030 | 7/1970 | Germany | 73/37 |

*Primary Examiner*—Richard C. Queisser
*Assistant Examiner*—Joseph W. Roskos
*Attorney, Agent, or Firm*—Pennie & Edmonds

[57] ABSTRACT

An apparatus for testing hollow bodies comprises a frame, a testing head mounted in the frame for axial motion with respect to and rotation about an axis, means for supporting at least one of the hollow bodies in axial alignment with the testing head and in a fixed position with respect to the axis during rotation of the testing head, means for imposing an axial motion to the testing head upon rotation of the head, means for feeding to the supporting means successive bodies to be tested, and means for removing from the supporting means bodies which have been tested.

9 Claims, 3 Drawing Figures

APPARATUS FOR TESTING HOLLOW BODIES

The present invention relates to a testing apparatus for testing hollow bodies, and more particularly for examining, testing and checking hollow bodies such as bottles, containers or packing containers formed, for example, of plastic or other materials such as metal, glass, or the like.

Various processes for examining, testing or checking hollow bodies such as bottles, are already known. The hollow bodies are tested by applying to the mouth or neck of the hollow body a testing head which checks various features of the hollow body such as the geometry of the mouth, the dimensions of the hollow body, crushing resistance, gas-tightness, etc.

In one such prior art procedure the hollow bodies are moved beneath the testing head on a conveyor which is displaced intermittently, with the examination being carried out while the hollow body and the conveyor are both stationary. The operating rate of installations of this type is limited and, furthermore, the applicant has found that the results of the examination, tests or checking operations were often very inaccurate.

Testing devices have also been proposed wherein the hollow body is advanced continuously, the testing head being displaced with the hollow body over a specific distance and then being returned to its initial position where it comes into contact with another hollow body. However, these devices have not produced a marked improvement in the operating rate. Furthermore, they are complicated and require an especially complex control system.

The object of the present invention is to obviate these disadvantages and to provide an apparatus for testing hollow bodies which can be operated at exceptionally high operating speeds while insuring a high degree of precision during the testing process. In addition, the apparatus according to the invention is designed to be readily adaptable to test hollow bodies of different types and of different geometries. Furthermore, the apparatus of the invention can be easily incorporated in existing machines for manufacturing hollow bodies without requiring modification of the machine.

BRIEF SUMMARY OF THE INVENTION

In accordance with the present invention, the apparatus for testing hollow bodies and, more particularly, for testing hollow bodies formed of plastic material, for example, bottles, containers, or the like, comprises a frame, a testing head mounted in the frame for axial motion with respect to and rotation about an axis, means for supporting at least one of the hollow bodies in axial alignment with the head and in fixed position with respect to the axis during rotation of the head, means for imposing an axial motion to said head upon rotation thereof, means for feeding to the supporting means successive bodies to be tested, and means for removing from the supporting means bodies which have been tested.

In a preferred embodiment, the apparatus of the invention is carried by a frame equipped with vertically adjustable feet so that it can be positioned adjacent to a conveyor, for example, a conveyor belt, enabling it to pick up the hollow bodies disposed on the belt, to position them on the support means and then to return the hollow bodies to the conveyor downstream of the supplying position. The testing heads and supporting means may advantageously be supported on a vertical shaft journaled in the frame and driven by a drive means disposed therein. The upper end of the shaft is preferably journaled in a non-rotating housing supported by the frame, the housing bearing a cylindrical cam member cooperating with a cam follower coupled to the testing head to impose thereon a reciprocal axial motion upon rotation of the shaft and the head. The testing heads may advantageously be carried by a head support plate which is secured to the rotary shaft at an axially adjustable position thereon. The housing bearing the cam may also be mounted in the frame for axial movement with respect thereto.

The support means are advantageously designed to support hollow bodies of different dimensions and comprise at least one and preferably a plurality of star-shaped elements axially displaced from each other and secured to the shaft, the hollow body being gripped between the arms of the star-shaped elements. A circular plate is preferably mounted on the rotary shaft beneath the star-shaped elements, this plate being designed to receive the base of the hollow body. In order to prevent radial displacement of the bodies under the influence of centrifugal force during rotation, a circular rail can be provided about the periphery of the plate.

The geometrical dimensions of the star-shaped element or elements, i.e. the spacing of their arms and their configuration, are adapted to the cross section of the hollow bodies held between the arms so as to prevent any substantial displacement of the hollow bodies relative to said star-shaped elements. The arms of the star-shaped elements and the central part thereof may be provided with rollers which cooperate with the hollow bodies when the latter have a circular cross section.

The means for supplying and removing the hollow bodies advantageously consist of additional star-shaped elements which are mounted on vertical rotary shafts. One of these star-shaped elements is designed to pick up a hollow body from the conveyor and supply it to the star-shaped elements the support and the other is designed to return a hollow body from the star-shaped elements to the conveyor.

BRIEF DESCRIPTION OF THE DRAWING

Other objects, features and advantages of the present invention will be made apparent in the following description thereof which is provided by way of example only with reference to the accompanying drawings, in which.

DESCRIPTION OF PREFERRED EMBODIMENT

Figure 1:
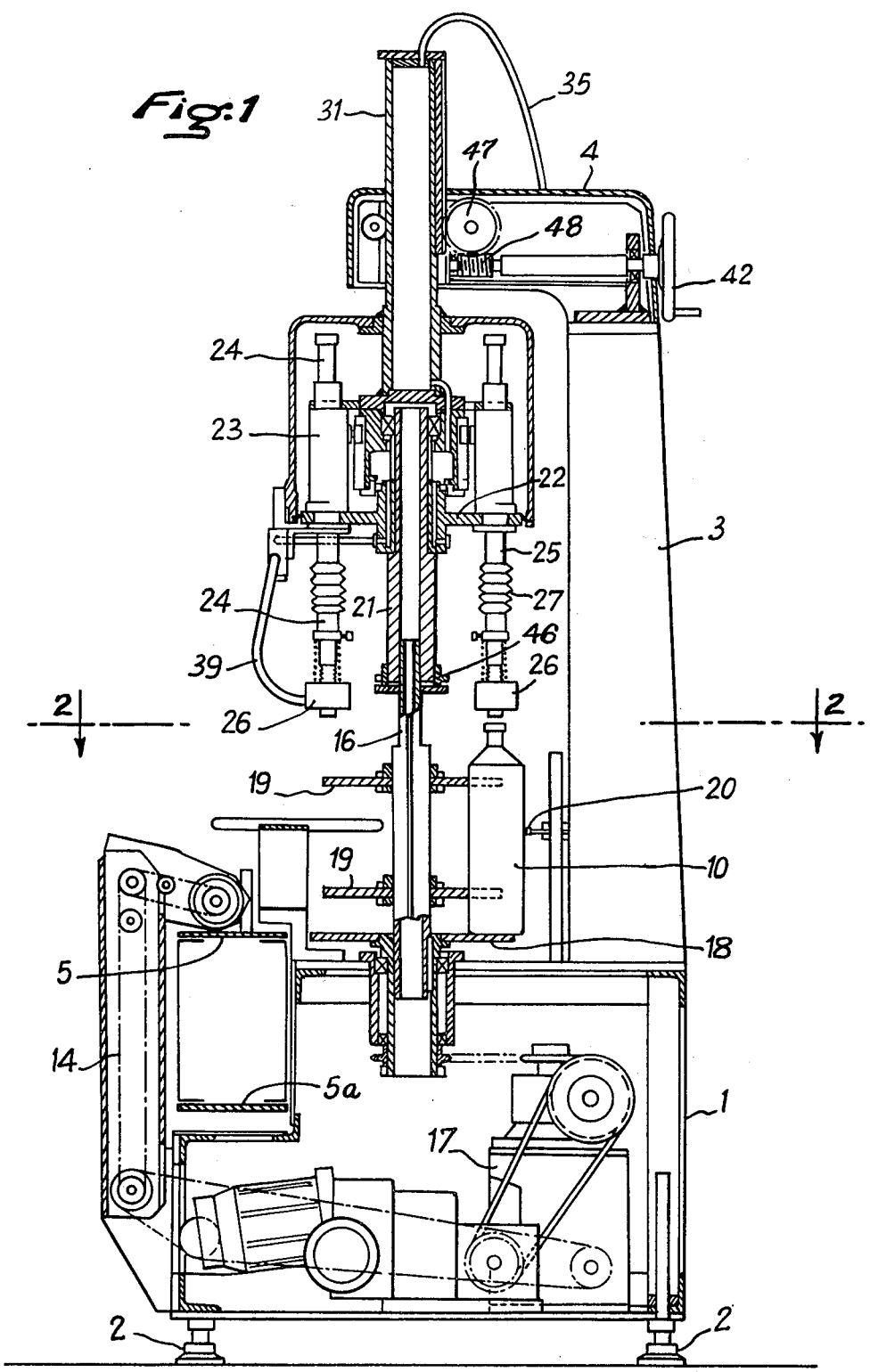
FIG. 1 is a vertical axial sectional view of an apparatus according to the invention.
Figure 2:
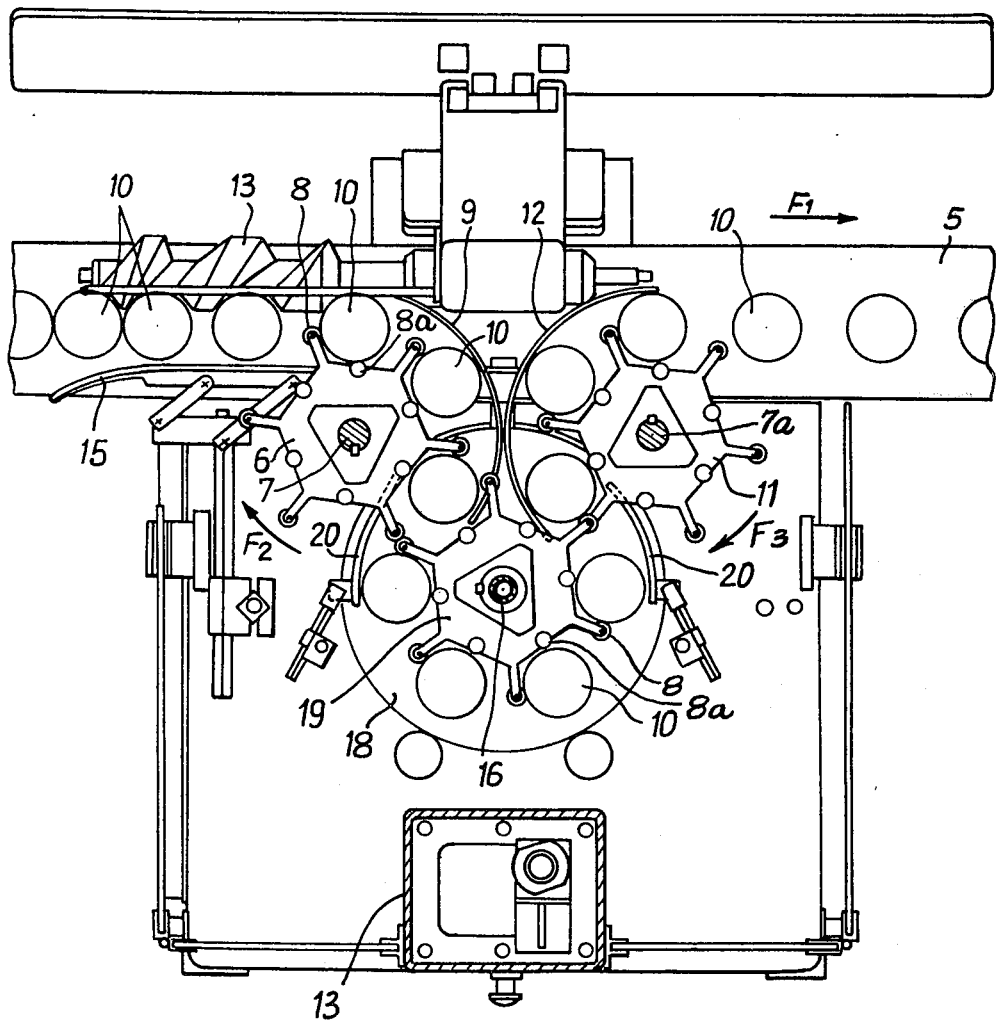
FIG. 2 is a transverse sectional view taken on the line 2—2 of FIG. 1.

Referring now to FIGS. 1 and 2, the testing apparatus there shown comprises a lower fram 1 mounted on vertically adjustable feet 2 and carrying a vertical member 3 which supports a horizontal cross-piece 4. The frame 1 is disposed adjacent an endless belt conveyor the upper and lower runs of which are shown at 5 and 5a respectively. Above the lower frame 1 and run 5 is disposed a first star-shaped feeding element 6 (FIG. 2) keyed to and rotating about a vertical shaft 7 in the direction of the arrow F2. The star-shaped element 6 has six arms each terminating in a roller 8, and additional rollers 8a are disposed in the hollows between the arms. The arms of element 6 extend above the run 5 of the conveyor belt, which is advanced in direction of the arrow F1 (FIG. 2), so that in cooperation with a semi-circular rail 9 extending above belt 5 they intercept plastic bottles 10 carried by belt 5 from left to right in FIG. 2. A second star-shaped element 11 substantially identical to the first is disposed above run 5 downstream of element 6 and is keyed to and rotates with a vertical shaft 7a in direction F3.

To enable the bottles 10 to be gripped by the star-shaped element 6, a horizontal endless screw 13 driven in rotation, for example, by a motor mounted in the frame 1 through the intermediary of transmission means 14 such as chains or the like, is advantageously disposed above the conveyor belt. The screw 13 cooperates with a longitudinal rail 15 disposed above the conveyor belt 5 to successively feed to the star-shaped element 6 bottles at well defined intervals.

The apparatus also includes a main vertical drive shaft 16 driven through the intermediary of suitable means by way of a motor reducer unit 17 housed in the frame 1. The rate of rotation of the shaft 16 corresponds to the rate of rotation of the star-shaped elements 6 and 11.

The vertical shaft 16 supports a circular plate 18 which is disposed beneath but in partially overlapping relation to elements 6 and 11 so that the bottles moving along run 5 are engaged by element 6 and are deposited on the plate 18. The bottles deposited on the plate 18 after rotating about shaft 16 are engaged by star-shaped element 11 and in cooperation with rail 12 which is symmetrical with rail 9, they are in this way transferred back onto the conveyor downstream of element 6.

Two central star-shaped elements 19 each having six arms are disposed above the plate 18 at an adjustable distance therefrom and are secured to shaft 16. As shown in FIG. 2, the elements 19 are similar in shape to elements 6 and 11 and are also provided with idle rollers at the ends of the arms and in the hollows therebetween. Circular rail sections 20 are provided around the periphery of plate 18 for retaining the bottles on the plate 18 between the arms of the star-shaped elements 19 during rotation of the plate.

Thus, it will be seen that the bottles 10 are fed to plate 18 by the star-shaped element 6 and rotate with the plate 18 between pairs of adjacent arms of the elements 19, without being able to escape in a radial direction because of the disposition of the rails 20.

Figure 3:
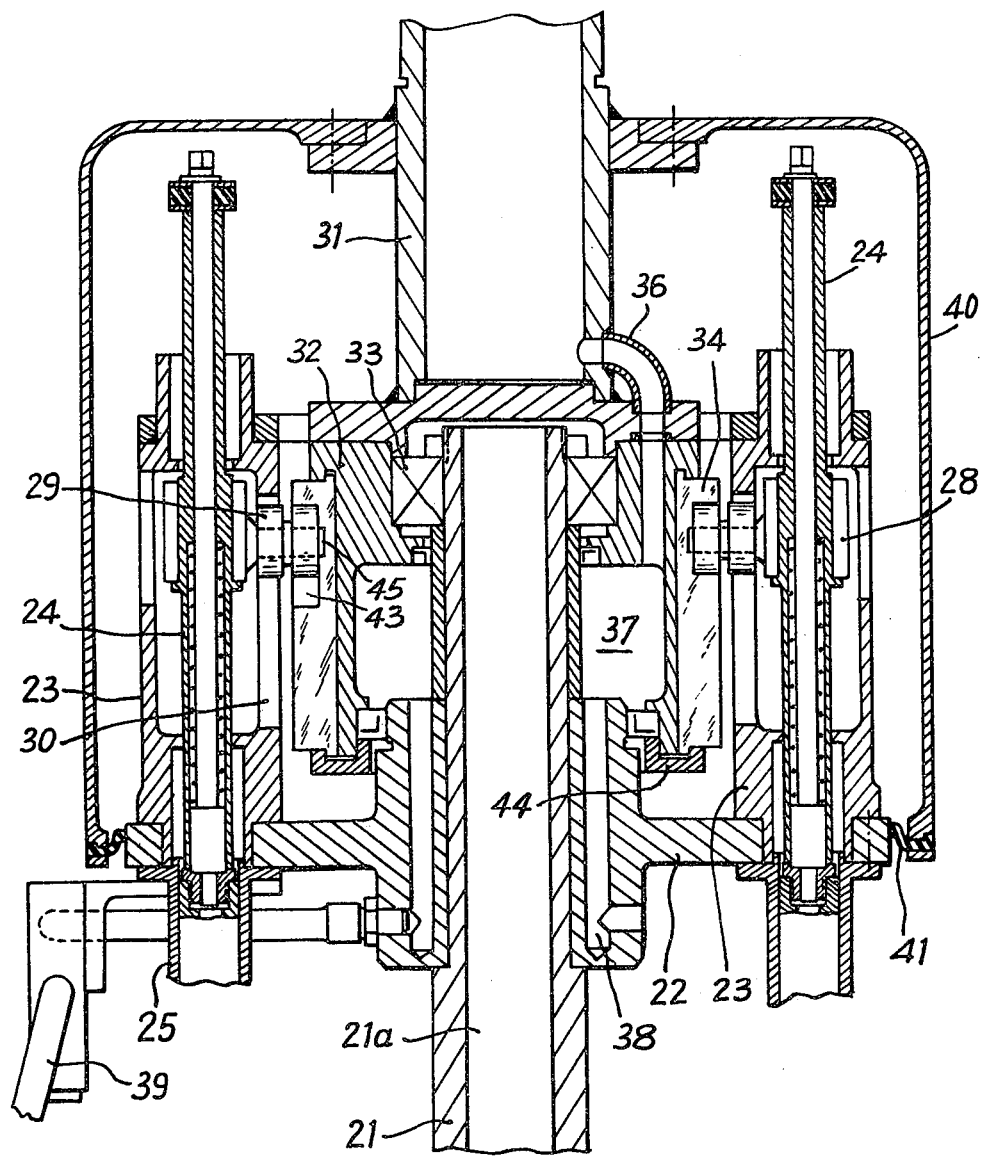
FIG. 3 is a fragmentary axial sectional view similar to that of FIG. 1, but shown at an enlarged scale.

As shown in FIGS. 1 and 3, the upper part 21 of the shaft 16 supports a plate 22 which is secured to the shaft 21 and which is provided with a plurality of openings in which are mounted a corresponding number of hollow cylindrical housings 23. The cylindrical housings 23 are each disposed above a position on plate 18 occupied by a bottle 10 thereon.

A shaft 24 is mounted for vertical motion within each housing 23, with the lower part of the shaft 24 extending in a cylindrical bushing 25 which forms an extension of the housing 23. The lower end of each shaft 24 supports a testing head 26 and, as shown in FIG. 1, a protection belows 27 is provided between the lower part of each shaft 24 and bushing 25. Inside housing 23 each shaft 24 is provided with a collar 28 to which is affixed a horizontal shaft 45 which extends beyond the housing 23 towards shaft 21 through a vertical elongated slot 30 in the side of the housing 23. On the end of each shaft 45 is mounted a follower roller 29.

The cross-piece 4 supports a non-rotatable vertical shaft 31 above the end of and coaxially with respect to the upper shaft 21. To the lower end of shaft 31 is affixed a hollow tubular element 32 having a generally cylindrical exterior surface. The shaft 31 and element 32 form a housing into which shaft 21 extends and is journaled in a bearing 33 disposed therein.

About the exterior surface of element 32 is mounted a cylindrical cam member 34 held in place by ring 44 threaded onto the lower end of element 32. The exterior surface of cam member 32 has a groove 43 encircling member 34 at different levels to define a cam surface traversed by cam-follower rollers 29. Thus, it will be seen that rotation of shaft 16 will cause the plate 22, which is fixed to the upper end 21 of shaft 16, and the test heads 26 carried by the plate 22 to rotate therewith. At the same time, because the cam-follower rollers 29 follow the groove 43 in the surface of the stationary cam member 34, there is produced, during rotation of shaft 16, a vertical movement of the shafts 24 and the heads 26.

The heads 26 may be supplied with fluid, for example, with compressed air via a tube 35 to the interior of the hollow shaft 31 and through a curved conduit 36 situated at the base of the shaft 31, into an annular space 37 provided at the lower part of element 32. From the annular space 37 the compressed air is admitted to the conduits 38 in the rotary plate 22 and from there the air is fed to heads 26 through flexible conduits 39. A bell-shaped stationary cap 40 having for example, at its base, an annular seal 41 in rubbing contact with the periphery of the plate 22 can also be advantageousy mounted on the shaft 31.

The pressure fluid can be supplied to the testing heads from a source disposed, for example, inside the frame 1, the source being connected to conduit 35 by a fluid line (not shown) extending along vertical member 3 and the cross-piece 4.

The testing or check heads 26 can be of any known type which is suitable for the testing operation to be carried out on the hollow bodies. The testing heads can, for example, be of a type which can simultaneously check the tightness and crushing resistance of a plastic bottle. They can also be of a type having a number of different parts which are movable with respect to one another and which have a predetermined relationship such that when a bottle under test is without flaws, lights mounted on the movable parts are aligned with stationary photoelectric cells. If on the other hand, the hollow body under test has a flaw, at least one of the lights will not be aligned with an associated cell causing the cell to signal the presence of a defective bottle. The movable parts of the testing head can also be such that the parts will be aligned and permit light from a stationary light source mounted, for example, on the cross piece to pass to a stationary photo electric cell only when the body under test is without defects.

In operation of the testing apparatus, the bottles 10 are supplied from the conveyor run 5 by the star-shaped supply element 6 to the support comprising the plate 18 and the star-shaped elements 19. On the support the bottles 10 are disposed in a precise position in contact with the rear arm of the star-shaped element 19 with each bottle on the plate 18 being axially aligned beneath a head 26. Rotation of the plate by the shaft 16 causes the head 26 to be lowered and placed on the bottle. The head 26 then carries out the examining, testing or checking operations during part of the circular path of the plate 18. The head is then raised and the bottle is delivered to the star-shaped element 11 which returns it to the conveyor run 5.

Thus, the apparatus of the invention can be positioned adjacent to any conveyor belt in an existing system without requiring any modification of the system.

The central vertical shaft of the apparatus can advantageously be formed from two seperate parts, with the lower shaft 16 telescoping into the hollow upper shaft 21, the two shafts 16 and 21 being coupled together by a two-part collar 46. The non-rotatable shaft 31 is also advantageously mounted in cross-arm 4 for axial motion with respect thereto, the axial position of the shaft 31 being adjusted for example, by a rack system 47 mounted in cross-arm 4 and operated by an endless screw 48 rotated by handle 42. It will be seen that raising or lowering of the housing formed by shaft 31 and member 32 will also raise or lower shaft 21 carried by member 32, and consequently the plate 22 affixed to shaft 21, with respect to plate 18 affixed to shaft 16. This arrangement provides a means for adjusting the axial distance between the plate 22 carrying the test heads 26 and plate 18, on which the bottles rest, in order to accommodate bottles of different heights.

When it is desired to modify the shape and dimensions of the hollow bodies to be tested it suffices to mount in place new star-shaped elements 19 adapted to the geometry of the different hollow bodies and if required the cam member 34 can also be replaced by a new cam part.

It is also possible to mount in position a new set of heads by disconnecting the end of the shaft 21 from the shaft 16 and by mounting a new shaft 21 with a different plate 22 having different heads.

The invention thus provides an apparatus for testing hollow bodies comprising a frame 1, a testing head 26 mounted in the frame 1 for axial motion with respect to and rotation about an axis, supporting means, such as the plate 18 and star-shaped element 19, which hold the hollow body or bodies in a fixed position with respect to the axis and in alignment with head 26 during rotation thereof. The apparatus also includes means for imposing an axial motion to the head 26, such as the cam member 34 and cam follower rollers 29, upon rotation of the head, means for feeding to the supporting means successive hollow bodies to be tested and means for removing from said supporting means bodies which have been tested such as the star-shaped shaped elements 6 and 11. The testing heads and supporting means of the apparatus may advantageously be supported on a vertical shaft rotatably mounted in the frame 1 and the apparatus may also include a non-rotatable housing, formed by shaft 31 and tubular element 32. The housing may advantageously be mounted on axial movement in the frame and provided with bearing means, such as bearing 31, in which the upper end of shaft 21 is journaled.

Although the present invention has been described in relation to a presently preferred embodiment, the invention itself is not limited thereto but rather comprehends all modifications of that embodiment properly falling within the spirit and scope of the appended claims.

I claim:

1. An apparatus for testing hollow bodies comprising a frame, a shaft mounted at one end for rotation in said frame, said shaft carrying means for supporting at least one of said bodies in a fixed position with respect to said shaft upon rotation thereof, a testing head axially displaced from said supporting means and mounted on said shaft in axial alignment with and for axial motion with respect to said position, a housing non-rotatably mounted in said frame coaxially with said shaft, and bearing means mounted in said housing for supporting the other end of said shaft, means for imposing an axial motion on said head upon rotation thereof, said means including a cam member mounted about said housing and a cam follower driven by said cam and coupled to said head, means for feeding to said supporting means successive bodies to be tested, and means for removing from said supporting means bodies which have been tested.

2. Apparatus according to claim 1 wherein said cam member has a cylindrical exterior surface which is substantially coaxial with said shaft and a groove extending about said surface, said groove defining a cam surface imparting to said cam follower an axial reciprocating motion upon rotation of said head.

3. Apparatus according to claim 1 wherein said housing is mounted in said frame for axial motion with respect thereto.

4. Apparatus according to claim 1 wherein said shaft is formed of at least two separable parts, one of said parts supporting said testing head and the other of said parts carrying said supporting means.

5. Apparatus according to claim 1 further including means to supply pressure fluid to said head.

6. In an apparatus for testing hollow bodies moving along a conveyor and having a frame, a vertically extending drive shaft mounted at its lower end for rotation in said frame, a support plate attached to the lower end of said drive shaft for rotation therewith at a location adjacent to said conveyor, means for successively moving hollow bodies from said conveyor onto said support plate for movement about said axis and for thereafter moving the hollow bodies from the support plate and back onto said conveyor, at least one testing head mounted on said drive shaft at a location spaced vertically above said support plate for rotation therewith in axial alignment with a hollow body supported on said plate and for simultaneous vertical movement into and out of engagement with the aligned hollow bodies, the improvement comprising:
   a. a hollow shaft fixed to said frame against rotation and extending coaxially of said drive shaft into telescoping relation with its upper end;
   b. bearing means coupling said drive shaft to said hollow shaft for rotation relative thereto;
   c. a stationary cam fixed to said hollow shaft and having a cam surface extending around the axis of rotation of the drive shaft; and
   d. cam follower means fixed to each of said testing heads and engaging said cam as the testing heads are rotated for effecting the vertical movement thereof.

7. The improvement in the testing apparatus according to claim 6 further comprising:
   a. control means coupling said hollow shaft to said frame for vertical adjustment of its position relative to said conveyor; and
   b. said drive shaft includes:

1. an upper part supporting said testing heads and connected to said hollow shaft for vertical movement therewith, and
2. a lower part on which said support plate is mounted, said lower part being mounted in said frame against vertical movement.

8. The improvement in the testing apparatus according to claim 6 wherein:
   a. said cam comprises a cylindrical member fixed coaxially to said hollow shaft; and
   b. said cam surface is defined by a groove in the outer surface of said cylindrical member.

9. The improvement in the testing apparatus according to claim 8 further comprising:

a. first conduit means for connecting said hollow shaft to a source of pressure;
   b. second conduit means connecting said hollow shaft to the interior of said cylindrical member, said cylindrical member being telescoped over said drive shaft and having an interior surface spaced therefrom to provide an annular space;
   c. a support plate for said testing heads fixed at the upper end of the drive shaft and having a collar portion telescoped into said annular space in rotatable relation with the cylindrical member; and
   d. third conduit means extending through said collar portion for placing each of said testing heads in fluid communication with said annular space.

* * * * *